United States Patent [19]

Topp et al.

[11] Patent Number: 5,574,376
[45] Date of Patent: *Nov. 12, 1996

[54] A.C. FIELD MEASUREMENT SYSTEM FOR DETECTING AND SIZING DEFECTS IN A CONDUCTOR VIA FIXED ORTHOGONAL COILS

[75] Inventors: David A. Topp; Martin C. Lugg, both of Milton Keynes, England

[73] Assignee: Technical Software Consultants Limited, Milton Keynes, England

[*] Notice: The portion of the term of this patent subsequent to Oct. 12, 2012, has been disclaimed.

[21] Appl. No.: 84,228

[22] PCT Filed: Oct. 1, 1992

[86] PCT No.: PCT/GB92/00053

§ 371 Date: Jul. 6, 1993

§ 102(e) Date: Jul. 6, 1993

[87] PCT Pub. No.: WO92/12422

PCT Pub. Date: Jul. 23, 1992

[30] Foreign Application Priority Data

Jan. 11, 1991 [GB] United Kingdom .................. 9100589

[51] Int. Cl.[6] .................................. G01N 27/90
[52] U.S. Cl. .................... 324/529; 324/238; 324/242
[58] Field of Search .................................. 324/237, 238, 324/232, 242, 243, 529

[56] References Cited

U.S. PATENT DOCUMENTS

| | | | |
|---|---|---|---|
| 3,609,521 | 9/1971 | Desbrandes | 324/343 |
| 3,702,934 | 11/1972 | Jakobsen | 250/52 |
| 3,875,502 | 4/1975 | Neumaier | 324/241 |
| 4,594,549 | 1/1986 | Smith et al. | 324/232 |
| 4,761,610 | 8/1988 | Svegander et al. | 324/227 |
| 4,763,070 | 8/1988 | Hüschelrath | 324/225 |
| 4,924,181 | 5/1990 | Hüschelrath | 324/235 |
| 5,130,652 | 7/1992 | Kawakami et al. | 324/238 |

FOREIGN PATENT DOCUMENTS

| | | |
|---|---|---|
| 0090482 | 10/1983 | European Pat. Off. . |
| 0176932 | 12/1986 | European Pat. Off. . |
| 0299443 | 1/1989 | European Pat. Off. . |
| 395763 | 11/1971 | U.S.S.R. ............ 324/242 |

Primary Examiner—Kenneth A. Wieder
Assistant Examiner—Christopher Tobin
Attorney, Agent, or Firm—Panitch Schwarze Jacobs & Nadel, P.C.

[57] ABSTRACT

An a.c. field measurement testing system for detecting and sizing defects in a conductor includes a probe head having field coils located on a yoke so as to induce an a.c. field in the conductor and sensor coils arranged such that central longitudinal axes of the sensor coils are orthogonal one to another. The coils are wound on a former at the same location on the former and one of the sensor coils is oriented so that a longitudinal axis thereof is parallel to the induced a.c. field.

10 Claims, 3 Drawing Sheets

A.C. FIELD MEASUREMENT SYSTEM FOR DETECTING AND SIZING DEFECTS IN A CONDUCTOR VIA FIXED ORTHOGONAL COILS

This invention relates to an a.c. field measurement system for detecting and sizing defects in a conductor.

The techniques currently in use for the detection and sizing of surface-breaking cracks on ferritic steel structures require access to the bright metal. It is therefore necessary to carry out extensive pre-cleaning of the area to be inspected. This is particularly onerous underwater where marine growth and calcareous deposits have to be removed as well as oxide layers prior to inspection. Any protective paint layer present also has to be removed and then reapplied after inspection. Magnetic particle inspection (MPI) is then commonly used for crack detection and crack length measurement, possibly followed by a.c. potential drop (ACPD) inspection if crack depth information is required but more often material is removed by grinding until the MPI indication disappears. The a.c. field measurement (ACFM) technique was developed to extend the crack sizing capability of ACPD to a non-contacting form capable of inspecting through the non-conducting coatings. ACFM therefore differs from ACPD only by its measurement of above surface magnetic fields instead of surface potential differences. As long as the surface current density induced into the specimen is locally of uniform strength and direction, theoretical modelling of the expected magnetic fields above a defect is possible which allows crack sizes to be estimated from experimental measurements. However, a problem associated with ACFM is that signals indicative of defects in a test piece are conditioned by the speed at which a probe is scanned relative to the test piece and it is often difficult to distinguish between cracks in a test piece and spurious signals resulting from probe lift off.

According to the present invention there is provided an a.c. field measurement system for detecting and sizing defects in a conductor comprising a probe and a processor including at least one display, the probe including a yoke for inducing a uniform a.c. field in a first direction, sensor means comprising at least two coils a first coil of which having a longitudinal axis extending in the said first direction and a second coil of which having a longitudinal axis extending in a second direction orthogonal to the first direction and means for effecting energisation of the field the arrangement being such that signals produced by the coils indicative of defects in a test piece, when the probe is located adjacent the test piece, are processed by the processor and plots of signal magnitude derived from at least two of the coils are recorded on the display as a function of time or against each other.

The present invention is designed to implement a practical application of the ACFM technique by a combination of novel probe and graphical display formats. The probe is designed to achieve the two requirements of ACFM by the production of a locally uniform input current, perpendicular to the expected crack edge, and by the simultaneous measurement of at least two mutually perpendicular components of magnetic field at the same point in space. The technique can also be implemented with an array of double coil measurements, to give instantaneous display of the surface magnetic field distribution, or with controlled probe motion to give improved spatial resolution. The remote graphical display combines the conventional time-base plots of the individual magnetic field component strengths with a novel display format in which one component is used as the abscissa and another as the ordinate. This format, which has been dubbed a "butterfly plot" because of the characteristic shape produced by a crack, has several practical advantages for crack detection. Firstly, the removal of the time-base gives a display independent of the speed at which the probe is scanned and which can be retraced for confirmation. Secondly, the simultaneous monitoring of two components helps to distinguish between cracks and spurious indications due to probe lift-off. The combination of point measurements of magnetic field components and "butterfly plot" format allow multidimensional threshold boxes to be used to simplify or automate the detection process. It is also highly advantageous to be able to store the traces and replay them at a later date.

The ferromagnetic yoke is used to induce a current into the test piece while at the same time minimising the amount of direct induction into the sense coils. This is necessary to allow comparison of experimental readings with those theoretically predicted, and is achieved because the bulk of the magnetic field is channelled thorough the pole pieces onto the test piece underneath which completes the magnetic path.

A current sheet is thereby induced in the test piece in a direction normal to the line joining the pole pieces, the current density being approximately uniform over a large percentage of the area directly under the yoke. The sensing elements are sited midway between the pole pieces close to the test piece in a region of optimum field uniformity and consist of at least two coils wound one on top of another centered on a single point in space. These coils are "x-oriented", i.e. with an axis parallel to the line joining the pole pieces, and "z-oriented", i.e. with an axis normal to the surface of the test piece. A third coil may be provided "y-oriented", i.e. with an axis perpendicular to the line joining the pole pieces and parallel to the surface of the test piece. Theoretical modelling has shown that an x-oriented coil measures the background field strength which is reduced in the presence of a surface breaking defect going the whole length of the defect, a z-oriented coil measures a positive-going peak (or crest) in field strength above one crack end and a negative-going peak (or trough) above the other end, and a y-oriented coil measures a signal similar to a z-oriented coil but which reverses sign on traversing the plane of the crack. The coils may be of a circular or polygonal cross-section with dimensions small enough to allow good spatial resolution of the magnetic fields but large enough to enable local variations in geometry or lift-off to be smoothed out. Experience has found that diameters between 1 mm and 10 mm are desirable. The coils may be wound in either absolute or differential mode, the latter with two halves of the windings would be in opposite senses. The spacing between the poles of the yoke should be large enough to allow a reasonable area of uniform field strength but small enough to cope with curvature and other geometry effects in the test piece. Again, experience has found that spacing of between 25 mm and 75 mm is ideal. The height of the ends of the pole pieces above the base of the probe should be small enough to minimise direct induction into the sense coils but not so small that small changes in lift-off cause large variations in input field strength. Experience has found that a height between 5 mm and 20 mm is ideal.

The invention will now be further described, by way of example only, and with reference to the accompanying drawings in which.

Figure 1:
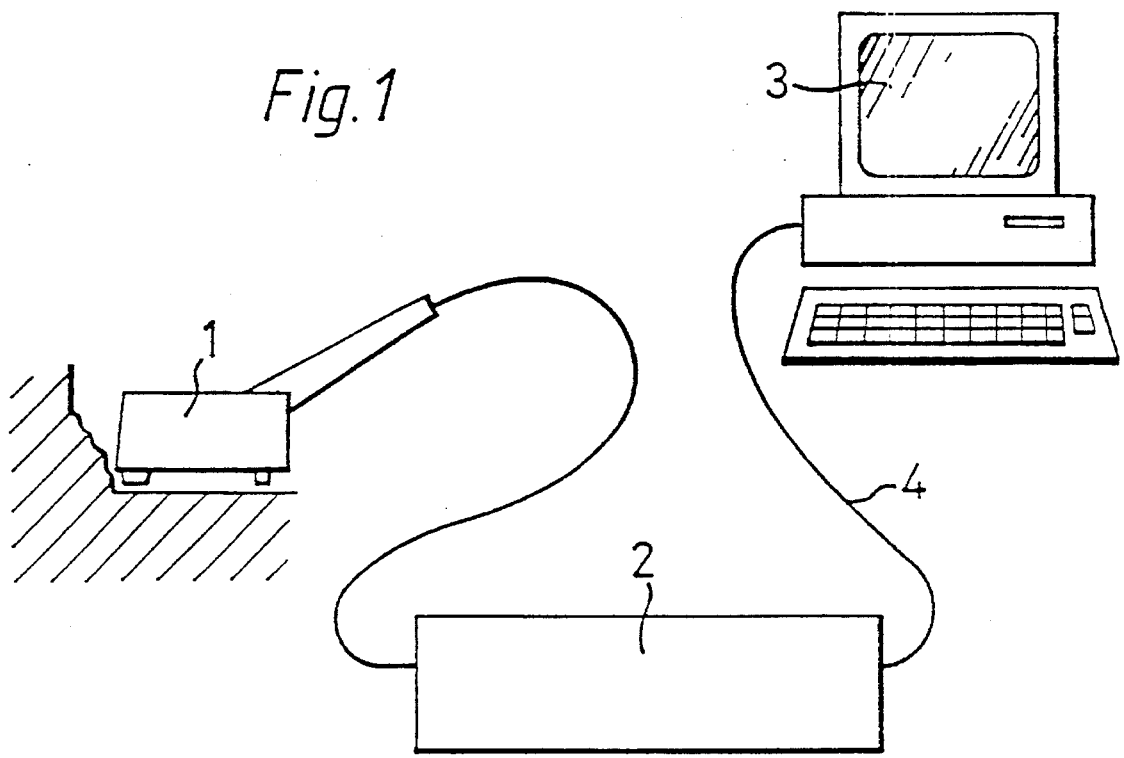
FIG. 1 is a schematic view of one embodiment of an a.c. field measurement testing system in accordance with the invention.

Referring to FIG. 1, the ACFM testing system of the present invention makes use of an ACFM Crack Microgauge 2. This may be housed in a watertight enclosure for subsea operation.

This unit outputs the drive current to the yoke in probe head 1 and amplifies, filters and rectifies the signals from the sense coils in the probe head 1. The signals are then transmitted via a serial communication line in an umbilical cable 4 to a computer 3.

The probe head 1 consists of a housing approximately 50 mm wide by 25 mm deep by 25 mm high to which is attached a handle approximately 75 mm long. Referring now to FIG. 2a which is an end view of the layout of the probe head, the sensing element is housed in a cylindrical dimple 5 protruding from a base. Two stainless steel legs, 6, also protrude from the base to permit the probe to accommodate a range of curvatures in the test pieces. The sense element is located as close to a front of the probe head as possible to allow it to be located as close to a weld toe as possible.

Figure 2C:
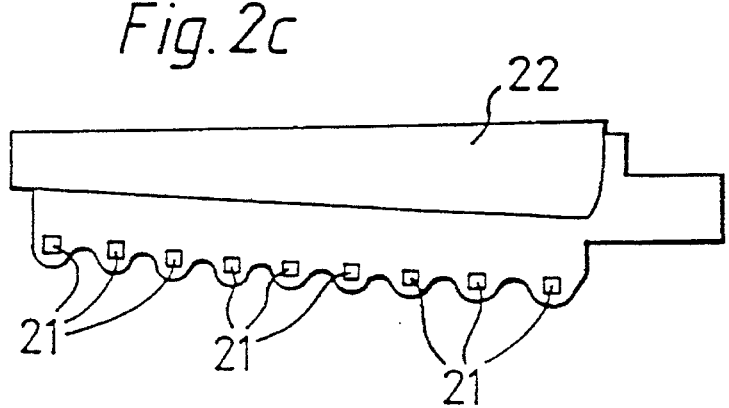
FIG. 2c is a side view of an alternative probe head containing an array of sensing elements.
Figure 2A:
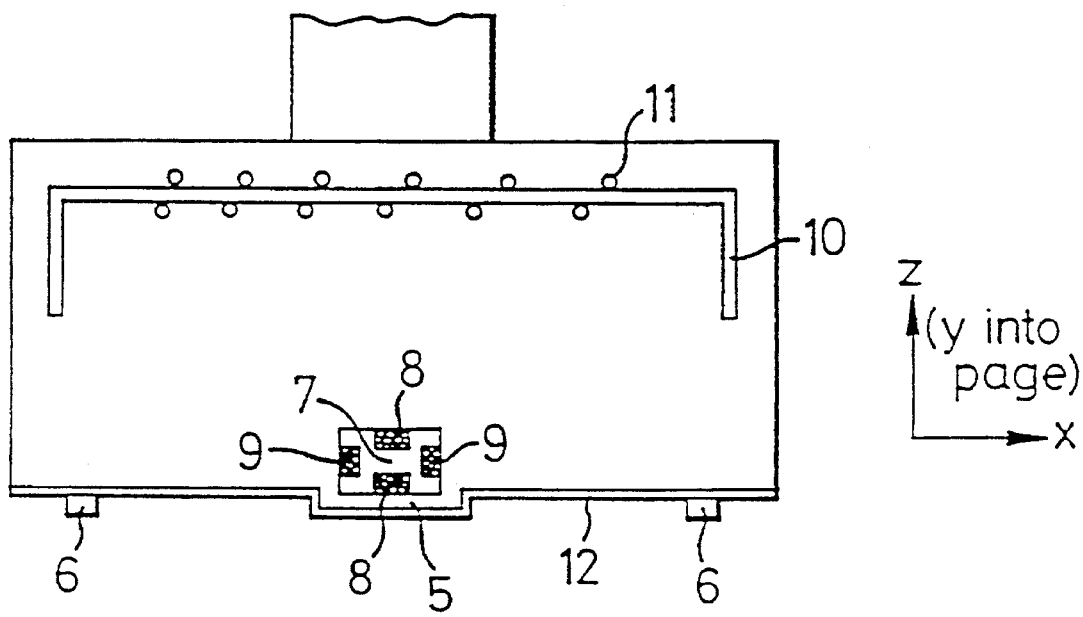
FIG. 2a is an end view of a probe head of the system.
Figure 2B:
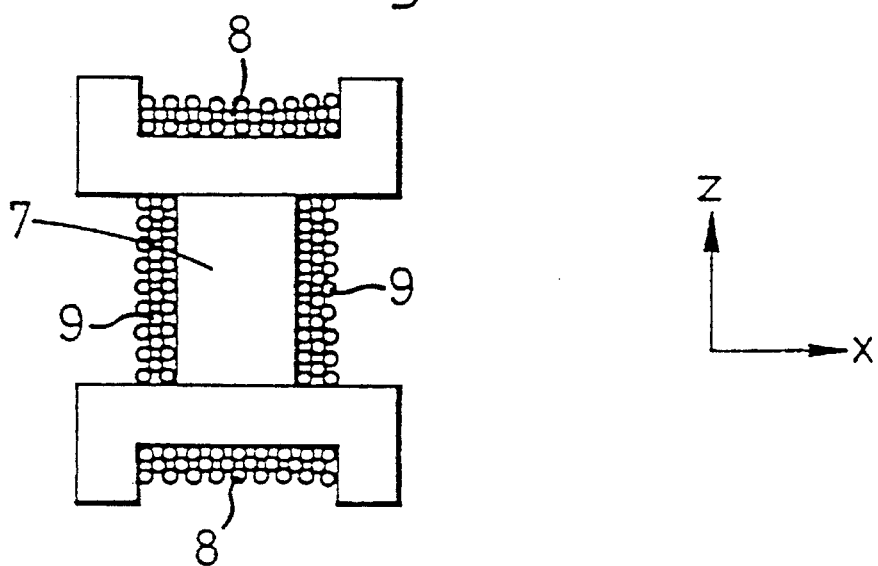
FIG. 2b is a detailed view of a sensing element located in the probe head.

The sensing element is shown in FIG. 2b and comprises two absolute coils wound around a common central point, 7. One coil, 8, is x-oriented, while the other coil, 9, is z-oriented. The x-oriented coil consists of 50 turns of 0.07 mm diameter enamel coated copper wire and has a square cross-section of side 5 mm. The z-oriented coil consists of 100 turns of the same wire and has a circular cross-section of diameter 3 mm. The excitation yoke, 10, is shown in FIG. 2a and comprises a thin flat mild steel plate with two ends bent through 90 degrees into a plane orthogonal to the base of the probe. Several turns of 1 mm diameter PVC coated copper wire, 11, carrying a 1.0 A current at 5 kHz are wound around the mid section of the yoke.

A stainless steel plate, 12, 0.5 mm thick, is fixed to the base of the probe to minimise wear. The thickness of this plate is small compared to the skin depth in stainless steel at 5 kHz, so that the magnetic fields passing through the sense coils are essentially unaffected.

The electronic instrumentation consists of a twin channel input amplifier module in which the voltages induced in the two coils are sampled alternately at a rate of 100 Hz via a solid state relay. This rate is sufficient to give almost simultaneous monitoring of the two channels. The signals are filtered and passed through a phase-sensitive detector which is preset to the phase of the background field measured by the x-oriented coil away from a defect. The instrument contains a microprocessor which controls sensor selection, gain selection, analog to digital conversion of the signals and communication with the computer via a serial link. The in-air version of the instrument also contains a simple keypad and display for control without the need for a computer. The underwater version of the instrument contains no external controls, but has a simple graphical display on a flying lead.

A menu-driven software program is used to control the acquisition, display, storage and interpretation of readings taken from the instrument. The user-friendly program incorporates automatic scaling of graphical displays, control of sampling rates and threshold values and storage of data in a form compatible with a standard spreadsheet package including a facility for attaching half a screen of descriptive text. Chosen parameter settings can be stored and recalled as required, and previously recorded data can be replayed.

Figure 3:
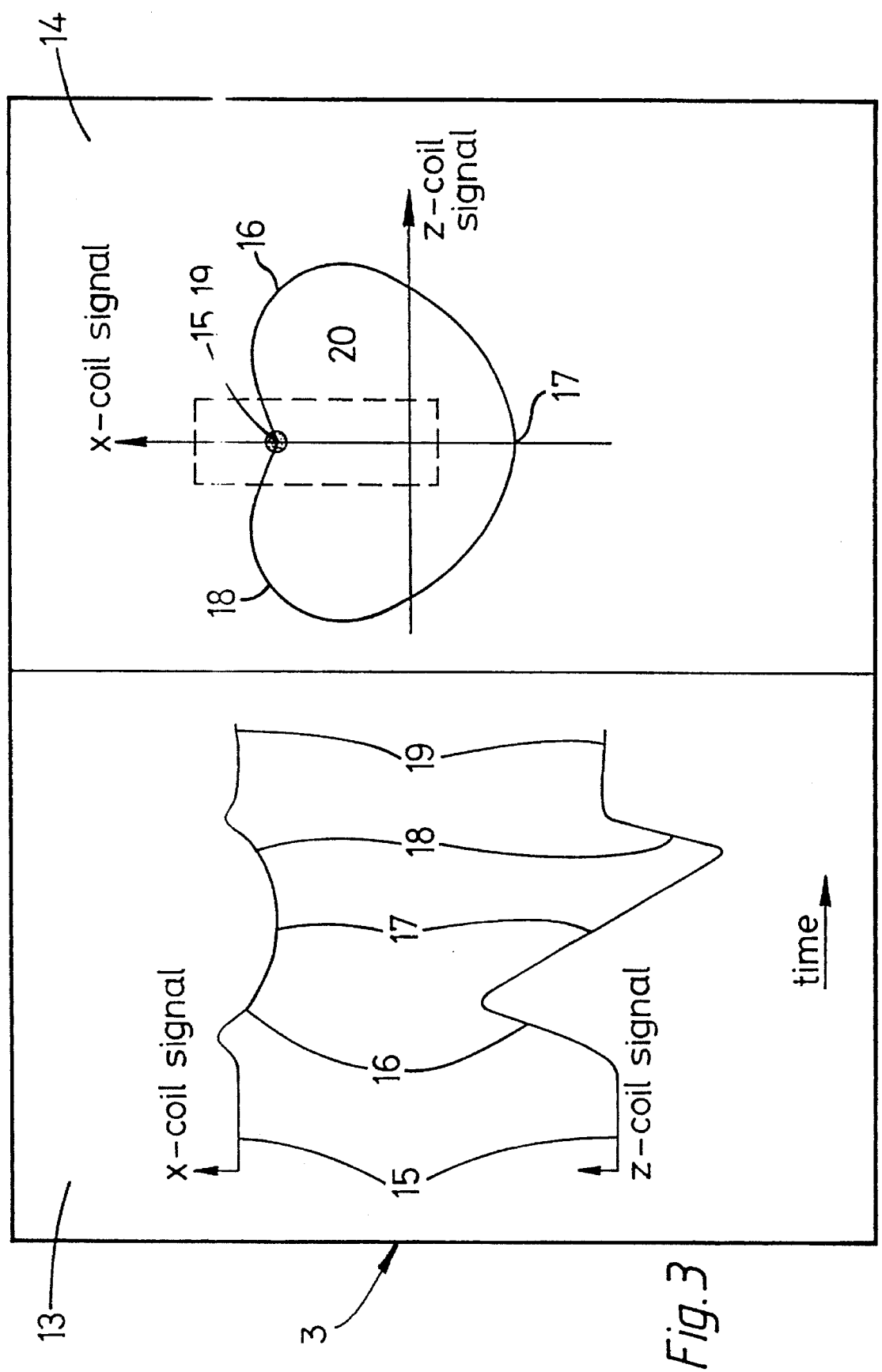
FIG. 3 is a representation of a graphical display of the system showing examples of timebase and "butterfly" plots arising from a surface breaking defect.

Referring now to FIG. 3, which is a representation of one form of graphical display on the VDU of the voltages plotted as they are received from the system described above, the left hand side of the screen, 13, contains plots of signal strength versus time for each of the two sense coils contained in the probe head, while the right hand side, 14, simultaneously records the signal strength from the x-oriented coil versus the signal strength from the z-oriented coil (i.e. the "butterfly" plot). The recordings shown in FIG. 3 represent typical displays resulting when the probe head is traversed along a simple surface-breaking crack. On the three traces shown, points 15 represent the start of each trace, points 16 mark the start of the crack, points 17 mark the midpoint of the crack, points 18 mark the end of the crack, and points 19 mark the end of each trace. In order for a crack to be differentiated from other variations in signal arising from probe lift-off or local geometry changes, threshold limits are required on the signals from both sense coils simultaneously. This is conveniently done in the "butterfly" plot, 14, by the addition of a two-dimensional threshold area, 20. Variations of signal that remain inside this area are ignored, but excursions of the trace outside this area result in the triggering of a warning that is transmitted to the operator by both audible and visible means. Confirmation of such a feature may be achieved by reversing the direction of probe movement which will result in the retracing of the "butterfly" plot in the opposite sense. The retracing is possible with a hand-held probe head because of the shape and size of the "butterfly". This retracing plot is independent of the speed of probe movement.

A second example of a possible application of the invention is shown in FIG. 2c which depicts a side view of an alternative probe head containing a one-dimensional array of sense elements for inspection of thread roots. The probe head has a thread form on one face to mate with the thread to be inspected. Each crown of this thread contains a pair of sense coils 21 located at a point as described previously. The ferromagnetic yoke 22 has a dimension of 50 mm between pole pieces and a length sufficient to cover all the sense elements. The sense coils 21 are connected such that, in operation of the system, each group of coils 21 is sampled in turn.

The electronic instrumentation required for operation of the probe is enlarged from that previously described to include a multi-channel input multiplexer with a corresponding increase in the complexity of controlling software and graphical display.

We claim:

1. An a.c. field measurement testing system for detecting and sizing defects in a conductor comprising a probe and a processor including at least one display wherein the probe includes a yoke for inducing a uniform a.c. field in a first direction, sensor means comprising at least two coils wound on a former at the same location on the former, said former being fixed in said probe with respect to said yoke and said first direction, a first coil of which having a longitudinal axis extending in said first direction and a second coil of which having a longitudinal axis extending in a second direction orthogonal to said first direction and means for effecting energisation of the a.c. field, the arrangement being such that signals produced by the coils indicative of defects in a test piece, when the probe is located adjacent to the test piece, are processed by the processor and plots of signal magnitude derived from at least two of the coils are recorded on the display.

2. A system as claimed in claim 1 wherein the yoke has a dimension from one pole to another of between 25 mm and 75 mm.

3. A system as claimed in claim 1 wherein each of the coils is of a diameter of between 1 mm and 10 mm.

4. A system as claimed in claim 1 wherein a surface of the probe which is intended to be located adjacent the test piece is of non-ferromagnetic material.

5. A system as claimed in claim 1, wherein the yoke comprises a rectilinear portion and pole pieces extending at right angles to the rectilinear portion.

6. A system as claimed in claim 1 wherein the sensor means is provided with a third coil a central longitudinal axis of which is orthogonal to the axes of the first and second coils.

7. A system as claimed in claim 1 wherein there is provided a plurality of sensor means.

8. A system as claimed in claim 1 wherein the sensor means are connected such that, in operation of the system, the sensor means are sampled sequentially.

9. A system as claimed in claim 1 wherein the signals produced by the coils are recorded on the display as a single plot, signal magnitude data from each coil being plotted with respect to signal magnitude data from each of the other coils.

10. A system as claimed in claim 1 wherein the signals produced by the coils are recorded on the display as plots of signal magnitude as a function of time.

* * * * *